(12) United States Patent
Altpeter et al.

(10) Patent No.: US 9,903,840 B2
(45) Date of Patent: Feb. 27, 2018

(54) METHOD FOR DETECTING TEMPORALLY VARYING THERMOMECHANICAL STRESSES AND/OR STRESS GRADIENTS OVER THE WALL THICKNESS OF METAL BODIES

(71) Applicant: AREVA GmbH, Erlangen (DE)

(72) Inventors: Iris Altpeter, Saarbrücken (DE); Ralf Tschuncky, Saarbrücken (DE); Hans-Georg Herrmann, Saarbrücken (DE); Jochen Kurz, Saarbrücken (DE); Gerd Dobmann, Dudweiler (DE); Gerhard Hübschen, Saarlouis (DE); Steffen Bergholz, Erlangen (DE); Jürgen Rudolph, Erlangen (DE)

(73) Assignee: AREVA GMBH, Erlangen (DE)

( * ) Notice: Subject to any disclaimer, the term of this patent is extended or adjusted under 35 U.S.C. 154(b) by 186 days.

(21) Appl. No.: 14/771,162

(22) PCT Filed: Feb. 20, 2014

(86) PCT No.: PCT/EP2014/000457
§ 371 (c)(1),
(2) Date: Aug. 27, 2015

(87) PCT Pub. No.: WO2014/131499
PCT Pub. Date: Sep. 4, 2014

(65) Prior Publication Data
US 2016/0003780 A1 Jan. 7, 2016

(30) Foreign Application Priority Data
Feb. 28, 2013 (DE) .................. 10 2013 003 500

(51) Int. Cl.
| | |
|---|---|
| *G01N 29/04* | (2006.01) |
| *G01N 29/24* | (2006.01) |
| *G01N 29/07* | (2006.01) |
| *G01N 29/11* | (2006.01) |
| *G01L 1/25* | (2006.01) |
| *G01M 5/00* | (2006.01) |
| *G01N 27/02* | (2006.01) |

(52) U.S. Cl.
CPC .......... *G01N 29/2412* (2013.01); *G01L 1/255* (2013.01); *G01M 5/0025* (2013.01);
(Continued)

(58) Field of Classification Search
CPC .... G01N 29/2412; G01N 29/07; G01N 29/11; G01N 29/227; G01N 29/30
See application file for complete search history.

(56) References Cited

U.S. PATENT DOCUMENTS

| | | | | |
|---|---|---|---|---|
| 2,892,914 A | * | 6/1959 | Rudd | ..................... B23K 13/00 |
| | | | | 200/85 R |
| 5,172,591 A | * | 12/1992 | Bohon | .................. E21B 43/127 |
| | | | | 73/152.55 |

(Continued)

FOREIGN PATENT DOCUMENTS

| | | |
|---|---|---|
| JP | 62-071855 | 4/1987 |
| JP | 02-071146 | 3/1990 |

(Continued)

OTHER PUBLICATIONS

International Application No. PCT/EP2014/000457 International Preliminary Report on Patentability dated Sep. 11, 2015 (8 Pages).

(Continued)

*Primary Examiner* — Helen Kwok
(74) *Attorney, Agent, or Firm* — Keller Jolley Preece

(57) ABSTRACT

The present invention relates to a method for detecting temporally varying thermomechanical stresses and/or stress gradients over the wall thickness of metal bodies, in particular pipelines. In the method, the temperature on the outer surface of the body is measured in order to determine a temperature progression and stress progression therefrom. In addition, electromagnetic ultrasonic transducers are used at at least one measuring point on the outer surface in order to determine the progression of the stresses and/or stress gra- (Continued)

dients over time over the wall thickness of the body in conjunction with the result of the temperature measurement. The method allows the fatigue monitoring of pipelines even in the event of rapid stress changes.

5 Claims, 7 Drawing Sheets

(52) U.S. Cl.
CPC ........ *G01M 5/0066* (2013.01); *G01N 27/025* (2013.01); *G01N 29/07* (2013.01); *G01N 29/11* (2013.01); *G01N 2203/0069* (2013.01); *G01N 2291/0258* (2013.01); *G01N 2291/02827* (2013.01); *G01N 2291/2634* (2013.01)

(56) References Cited

U.S. PATENT DOCUMENTS

| | | | | |
|---|---|---|---|---|
| 5,215,829 A | * | 6/1993 | Matsunobu | C21D 7/12 148/570 |
| 5,750,900 A | * | 5/1998 | Hugentobler | G01L 1/255 73/597 |
| 6,155,292 A | * | 12/2000 | Kurata | G01M 3/002 137/372 |
| 8,051,717 B2 | * | 11/2011 | Fukutomi | G01N 29/069 73/598 |
| 2005/0072236 A1 | * | 4/2005 | Heyman | G01N 29/07 73/602 |

FOREIGN PATENT DOCUMENTS

| | | |
|---|---|---|
| JP | 2002-181795 | 6/2002 |
| JP | 2008-261806 A | 10/2008 |
| JP | 2010-236892 | 10/2010 |
| WO | 2004/109222 A2 | 12/2004 |
| WO | 2011/138027 A1 | 11/2011 |

OTHER PUBLICATIONS

Rudolph, J. et al. AREVA Fatigue Concept—A Three Stage Approach to the Fatigue Assessment of Power Plant Components, Nuclear Power Plants, Dr. Soon Heung Chang (Ed.), InTech, Mar. 2012, pp. 293-316.
Office Action as received in Japanese Application 2015-559440 dated Jan. 9, 2018.

* cited by examiner

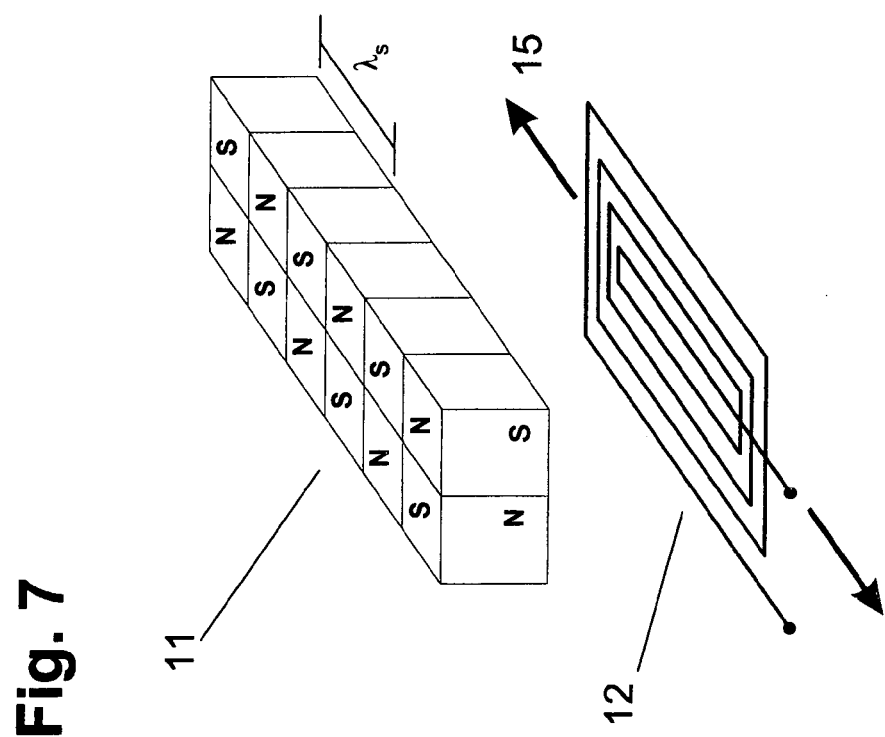

METHOD FOR DETECTING TEMPORALLY VARYING THERMOMECHANICAL STRESSES AND/OR STRESS GRADIENTS OVER THE WALL THICKNESS OF METAL BODIES

CROSS-REFERENCE TO RELATED APPLICATIONS

This application is a national phase entry under 35 U.S.C. § 371 of International Application No. PCT/EP2014/000457, filed Feb. 20, 2014, which claims the benefit of German Application No. 10 2013 003 500.7, filed Feb. 28, 2013. The entire contents of each of the foregoing patent applications are hereby incorporated by reference.

BACKGROUND OF THE INVENTION

Technical Area

The present invention relates to a method for detecting temporally varying thermomechanical stresses and/or stress gradients over the wall thickness of metal bodies, in particular pipelines, in which a surface temperature is measured at at least one measurement point on an external surface of the body, from which a temperature curve between the internal surface and the external surface is ascertained.

Detecting temporally varying thermomechanical stresses and/or stress gradients is of great significance above all on pipelines of atomic, conventional, and solar-thermal power plants, of chemical plants or also of wind power plants, since fatigue states of the respective component can be concluded from the temporal variation of the stresses or stress gradients, also referred to as stress-time series. The maximum stresses, which are responsible for aging of the components, generally occur on the internal surface of the pipelines or adjoining components, however, for example, due to rapid temperature changes of the medium flowing in the pipeline, so that direct measurement is not technically possible or is only feasible with disproportionally large expenditure.

Prior Art

For monitoring pipelines or other bodies for appearances of fatigue, inferring the stress-time series in the stressed parts via the measurement of the surface temperature on the external surface of the pipelines is known, for example, from J. Rudolph et al., "AREVA Fatigue Concept—A Three Stage Approach to the Fatigue Assessment of Power Plant Components" in: "Nuclear Power Plants", edited by Dr. Soon Heung Chang, KAIST Department of Nuclear & Quantum Engineering, South Korea, Publisher: InTech, Mar. 21, 2012, pages 293 to 316. In this case, the local stress is calculated from the measurement of the surface temperature via a finite element method.

However, specific rapid consequences of strain, which can arise, for example, due to transient mixing actions of cold and hot flows in the pipeline, and which cause temperature changes on the internal surface of the pipeline, can no longer be detected due to the measurement principle and therefore cannot be evaluated using such a technique. Such high-frequency mixing actions can also result in high levels of fatigue strains up to wall-penetrating cracks during operation as a result of the relevant frequency of occurrence of lower strain amplitudes.

A method for nondestructive material study is known from WO 2011/138027 A1, using which workpieces, which are subjected to high levels of mechanical and thermal strains, for example, pipelines in power plants, chemical plants, or refineries, can be studied with respect to occurring strain-related fatigue damage. In this method, two electromagnetic ultrasound transducers are used in a separate transmission-reception arrangement, to emit polarized ultrasound waves into the workpiece and to measure runtimes and amplitudes of the ultrasound waves both in pulse echo technology and also in sound transmission technology. Eddy current impedance measurements are also carried out in this case, to compare these measured variables to corresponding reference data. Possible changes in the microstructure of the wall of the workpiece can then be recognized by way of the comparison to the reference data. However, the method described therein does not enable the detection of temporally varying thermomechanical stress gradients over the wall thickness of pipelines.

WO 2004/109222 A2 describes a method for detecting material characteristics of metal bodies, in particular railway tracks, in which measurements are carried out using electromagnetic ultrasound transducers to determine the material characteristics, in particular the stress, density, or stiffness of the material. In addition, the temperature is measured at the measurement point to correct the ultrasound measurements on the basis of possible temperature effects.

U.S. Pat. No. 5,570,900 A describes a method for determining stresses on a workpiece with the aid of electromagnetic ultrasound transducers. This document substantially relates to the mechanical structure of the measuring unit, using which the ultrasound transducer is attached to the workpiece.

BRIEF SUMMARY OF THE INVENTION

The object of the present invention is to specify a method for detecting temporally varying thermomechanical stresses and/or stress gradients over the wall thickness of metal bodies, in particular pipelines, using which rapid stress changes over the wall thickness originating from the interior of the body can be detected from the external surface.

DESCRIPTION OF THE INVENTION

The object is achieved with the method according to patent claim 1. Advantageous embodiments of the method are the subject matter of the dependent patent claims or may be inferred from the following description and the exemplary embodiments.

In the proposed method for detecting temporally varying thermomechanical stresses and/or stress gradients over the wall thickness (over the cross section of the body or over the thickness of the pipeline wall) of metal bodies, two different measurement methods are combined. On the one hand, the surface temperature is measured on the external surface of the body, from which a temperature curve between the internal surface and the external surface is ascertained. On the other hand, in addition to this measurement, measurements are carried out using electromagnetic ultrasound transducers at at least one measurement point on the external surface, in order to determine the time curve of the stresses and/or stress gradients over the wall thickness of the body via the measured temperature and the temperature curve ascertained therefrom. The items of information required for the determination of the stresses and/or stress gradients are obtained in this case from a combination of the items of information obtained from the temperature measurement with the measurement data which were obtained using the electromagnetic ultrasound transducers. The stresses and/or stress gradients are preferably determined by analyzing ultrasound runtime, amplitude, and/or eddy current impedance measurements in conjunction with the temperature measurements.

The use of electromagnetic ultrasound transducers has the advantage that pipelines can therefore also be measured under operating conditions, for example, at temperatures greater than 200° C., in the event of radiation strains, or in the event of high operating pressures inside the body. In particular, electromagnetic ultrasound transducers offer the possibility of also detecting rapid stress changes, for example, caused by suddenly occurring temperature changes in the interior of the body, by way of rapid measurement data detection.

High-cycle fatigue (HCF) strain collectives may hereby also be identified and evaluated in principle. The ultrasound runtime measurements, amplitude measurements, and/or eddy current impedance measurements carried out in this case have the advantage that therefore strains on the internal surface of the body, which are not directly accessible, can also be detected. The ultrasound runtime and amplitude measurements can be carried out in this case in separate transmitter-receiver arrangement or in pulse echo technology or in a combination of both technologies. Furthermore, the transmission and reception amplitudes can also be logged and therefore can be used as an additional dimension in the analysis.

In the present method, by way of the additional measurement using electromagnetic ultrasound transducers, in particular using the ultrasound runtime, amplitude, and/or eddy current impedance measurements carried out thereby, the gaps with respect to rapid stress changes in the present solely temperature-based monitoring methods of pipelines are closed. In combination with temperature monitoring, these electromagnetic ultrasound testing methods expand the informative value of known fatigue monitoring systems. Therefore, high-frequency fatigue-relevant strain-time functions (stress-time series) may also be registered. Conclusions may thus be drawn about fatigue-relevant strains and therefore the time curve of the fatigue state of the respective body or pipe. By way of the use of electromagnetic ultrasound transducers, ultrasound runtime, amplitude, and eddy current impedance measurements may be combined in one sensor system or one testing head.

The fact is utilized in the proposed method that the data obtained from the temperature measurement, in particular the temperature curve and stress curve over the wall thickness of the body, which are derivable therefrom, can be used to determine the stresses or stress gradients over the wall thickness of the body, in particular in the case of high-frequency stress changes, from the measurement data of the ultrasound or eddy current measurements. Without the additional items of information from the temperature measurement, this would not be possible with the present accuracy, since the temperature influence on the ultrasound and eddy current impedance measurement data must be compensated for to obtain the accuracy.

The method and the embodiments thereof will be explained hereafter on the basis of the measurement or monitoring of pipelines. However, these explanations may readily also be transferred to other bodies.

A layer model is preferably used for the determination of the stresses or stress gradients. The stresses or stress gradients over the wall thickness of the pipeline are ascertained using this layer model in an iterative-numeric manner. The model is calibrated beforehand in this case while using the temperature measurement data and the items of information obtained therefrom, by measuring defined known realistic strains using the entire measurement system and detecting and archiving the obtained data. The temperature and stress curves over the wall thickness of the pipeline, which are approximated as constant piece by piece in the various layers, and also the temperature-corrected ultrasound runtimes, amplitudes, and eddy current impedances are specifically used as the model input variables for this purpose.

The layer model therefore supplies, as output variables, both layer-specific stress curves and also layer-specific ultrasound runtimes, amplitudes, and eddy current impedances, which are temperature-compensated. To be able to determine the stress curve in the pipeline wall rapidly in the application, the respective stress is inferred from the measured ultrasound runtimes, amplitudes, and eddy current impedances in the individual layers. To be able to ascertain this relationship between the stresses in the layers and the layer-specific ultrasound runtimes, amplitudes, and eddy current impedance values, an iterative optimization of the layer model is required. Two different procedures can be applied for the optimization.

The first procedure is based on a pattern recognition approach, which permits conclusions about the stresses in the individual layers with the aid of similarity comparisons. In this case, the layer-related stress curves are linked to the layer-related ultrasound runtime, amplitude, and eddy current impedance variables via algorithms, which relate the layer-related data to one another and therefore span a testing variable space of the layer-related variables. This multidimensional testing variable space is iteratively spanned in the optimization phase or during the calibration and is used thereafter to evaluate the real measurements with respect to their similarity in the spatial dimensions.

The second procedure is preferably a physical approach. It presumes the knowledge or ascertainment of the acoustoelastic constants of the pipe material at various operating temperatures and the electrical conductivities and enables the stress state to be ascertained therefrom for each layer by way of iterative adaptation of the model, by calculating the temperature-compensated ultrasound runtimes using the also temperature-compensated acoustoelastic constants and if necessary additionally also using the ultrasound amplitudes and eddy current impedances.

The advantage of the iterative optimization of the layer model based on physical laws or on a pattern recognition approach is the higher measurement speed and the immediate availability of items of information over the entire thickness of the pipe wall.

Furthermore, the iterative optimization enables the use of temporally preceding measurement data (history of the measurements) and measurement data at the analysis time (ultrasound and eddy current variables and also the instantaneous temperature on the outer wall) for increasing the accuracy of the model. In particular, the stresses or stress gradients on the pipe inner wall, which corresponds to the innermost layer of the layer model, are also obtained by use of this layer model.

Different arrangements and embodiments of the transducers are possible for the measurements using the electromagnetic ultrasound transducers. In principle, different combination transducers may be used as electromagnetic ultrasound transducers, for example, consisting of at least one HF coil and one electromagnet or one or more permanent magnets, wherein the HF coil can be used both for transmitting and/or receiving the electromagnetically excited ultrasound and also for eddy current impedance measurement. Furthermore, for example, combination transducers may also be used, which consist of at least two HF coils and one electromagnet or two HF coils and one or more permanent magnets. One HF coil is used in this case for transmitting and/or receiving the electromagnetically excited ultrasound and the other HF coil is used as a separate eddy current coil. The eddy current excitation can be performed using the same pulse as the generation of the ultrasound wave or also via a separate eddy current generator. Suitable ultrasound transducers are known to a person skilled in the art from the prior art.

Particularly advantageously, at least two electromagnetic ultrasound transducers are used at each measurement point, which operate with different polarization directions in pulse echo operation. The HF coil is used in these transducers both as the transmitting coil and also as the receiving coil. The transducers are designed or arranged so that they emit transverse waves, which are linearly polarized perpendicularly to one another, perpendicularly into the pipe. The transverse wave of one ultrasound transducer is preferably polarized in the axial direction of the pipe and the other is preferably polarized in the circumferential direction of the pipe. In this manner, the different stresses generated in these directions can be optimally detected.

In addition, two pairs of further electromagnetic ultrasound transducers are preferably used in separate transmission-reception arrangement at the respective measurement point. In these pairs, one transducer is used as the transmitter and the other as the receiver. These transducers can operate with two different wave types in sound transmission, both with Rayleigh transverse waves and also with horizontally polarized transverse waves. The two pairs of these additional electromagnetic ultrasound transducers are operated to detect the stress in the pipe wall using two polarizations oriented at 90° to one another, preferably in the axial direction and in the circumferential direction of the pipe. They are arranged in a cross shape for this purpose.

The possibility also exists of emitting differently polarized ultrasound waves into the pipe wall. Thus, for example, in the case of lesser wall thicknesses, instead of the Rayleigh wave or the horizontally polarized wave introduced in a glancing manner, a plate wave (SH/Lamb plate wave) can also be used. For perpendicular incident radiation, it is also possible to use radially polarized waves.

The ultrasound transducers, which are also referred to as testing heads hereafter, are preferably attached like a belt around the circumference of the pipe. The more densely this testing head arrangement is placed on the pipe along the circumference, the higher the lateral resolution for the stress determination along the pipe circumference.

Multiple testing belts having combination transducers may also be used simultaneously for additional redundancies. A variation of the testing head or transducer types for each belt also provides additional redundancy. Additional items of information can be obtained by using the data of different testing head types, different wave types, and/or different measurement frequencies.

In a further embodiment, which can be used in the case of ferromagnetic material of the pipeline, combination transducers having electromagnets are used, using which the hysteresis is modulated, to be able to measure the superimposition permeability (analysis of the permeability in the case of defined operating points or magnetic fields) and/or the dynamic magnetostriction (analysis of the ultrasound amplitude in the case of defined operating points or magnetic fields) as an additional surface-proximal variable.

BRIEF DESCRIPTION OF THE DRAWINGS

The proposed method will be explained in greater detail hereafter once again on the basis of an exemplary embodiment in conjunction with the drawings. In the figures:

FIG. 7 shows an example of the structure of a testing head for generating a horizontally polarized transverse wave.

EMBODIMENTS OF THE INVENTION

Figure 1:
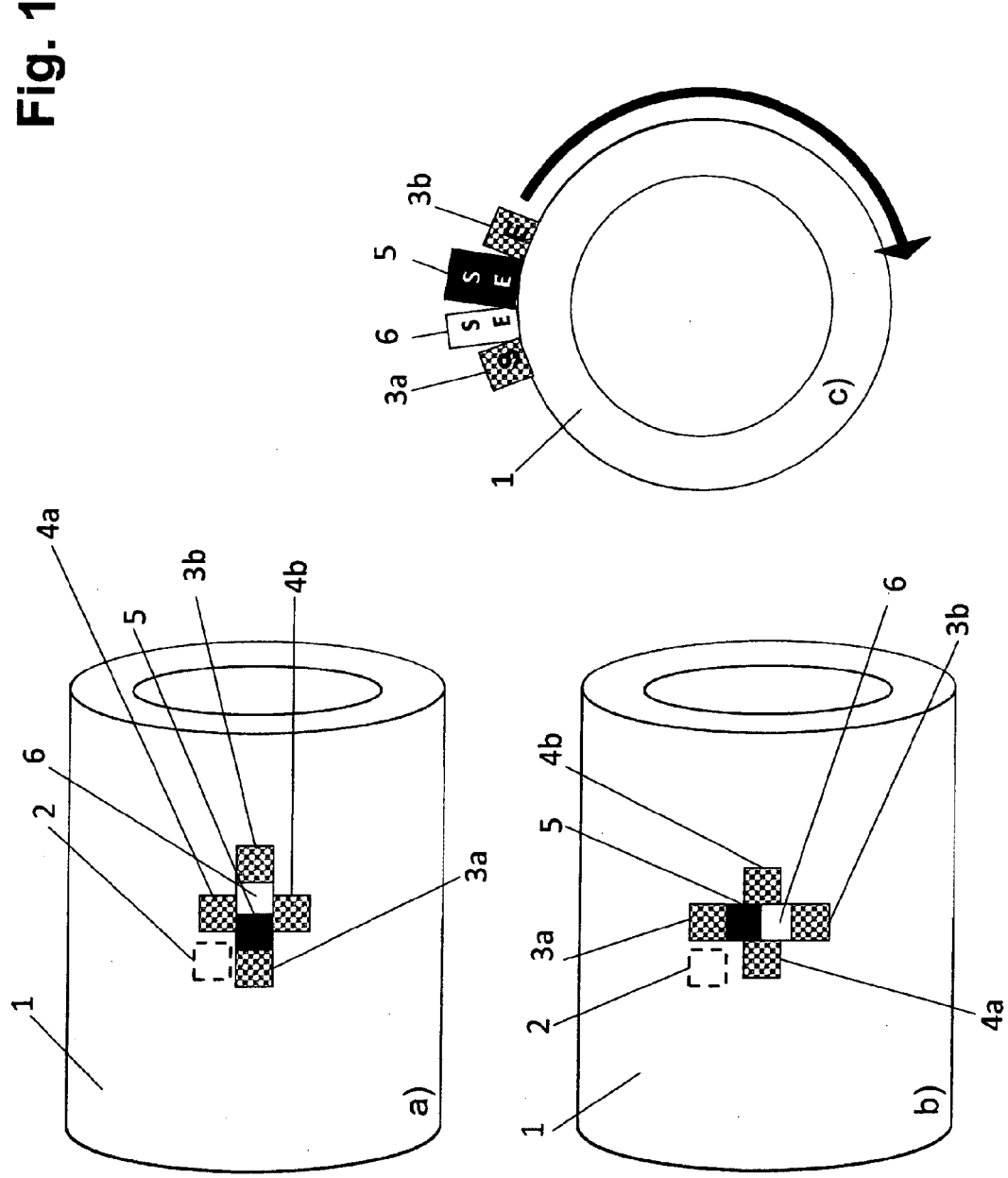
FIG. 1 shows two examples of the arrangement of the ultrasound testing heads on a measurement point according to one embodiment of the proposed method.

In the proposed method, the known temperature measurement for monitoring fatigue in a pipeline is combined with the measurement of ultrasound runtimes, amplitudes, and/or eddy current impedances in the pipeline wall, which is carried out using electromagnetic ultrasound transducers. The measurement points on the outer side of the pipe are selected in this case as needed. FIG. 1 shows a schematic illustration of a portion of a pipe 1, on the outer side of which a testing head arrangement for carrying out the ultrasound runtime, amplitude, and eddy current impedance measurements is illustrated. FIGS. 1a and 1b show two different possible arrangements in this case at the corresponding measurement point. The temperature sensor 2 used for the simultaneous measurement of the outer surface at this measurement point is also schematically indicated in the figure. This temperature sensor, for example, in the form of thermocouples, can also be integrated in the testing heads. Furthermore, multiple temperature sensors 2 can also be provided at each measurement point. The temperature measurement can also be performed immediately before or after the measurement using the ultrasound testing heads, of course.

It is clear from FIG. 1 that different ultrasound transducers or testing heads can be used for the ultrasound and/or eddy current measurements. In this case, these are separate transmission-reception arrangements having separate transmission and reception transducers 3a, 3b, 4a, 4b and integrated transmission-reception arrangements 5, 6, which operate in pulse echo operation. Using the separate transmission and reception transducers 3a, 3b or 4a, 4b, either Rayleigh waves or horizontally polarized transverse waves can be generated in the axial direction of the pipe wall. These testing heads operate in sound transmission, wherein the ultrasound waves are emitted from the transmitter 3a, 4a and, after propagation in the pipe wall in the axial direction of the pipe, are received again by the respective ultrasound transducer 3b, 4b. To detect the stress in the pipe wall, in this case two pairs of transmission transducers 3a, 4a and reception transducers 3b, 4b having polarizations oriented at 90° to one another—along the pipe axis and in the circumferential direction of the pipe—must be used for this purpose in each case. The two testing head pairs are arranged in a cross shape for this purpose, as is apparent from FIGS. 1a and 1b. The two further ultrasound transducers 5, 6 are integrated transmission and reception transducers, which emit linearly polarized transverse waves having different polarization directions (perpendicular to one another) perpendicularly into the pipe. In these transducers, the HF coil is used both for transmitting the ultrasound signals and also for receiving the ultrasound signals reflected on the pipe inner wall. One transducer 5 generates transverse waves which are polarized linearly in the circumferential direction of the pipe in this case, and the other transducer 6 generates transverse waves which are polarized linearly in the axial direction of the pipe. The eddy current impedance measurement can be carried out in a known manner via the integrated HF coils. Of course, combination transducers can also be used, in which an additional HF coil is provided for the eddy current impedance measurement. FIGS. 1a and 1b show different orientations or arrangements of the testing heads used, as they can be used in the present method. FIG. 1c once again shows an example of a section through the pipe having the corresponding attached testing heads. The testing heads are preferably used like a belt at different measurement points on the outer wall of the pipe, as is schematically indicated by the arrow in FIG. 1c.

Figure 2:
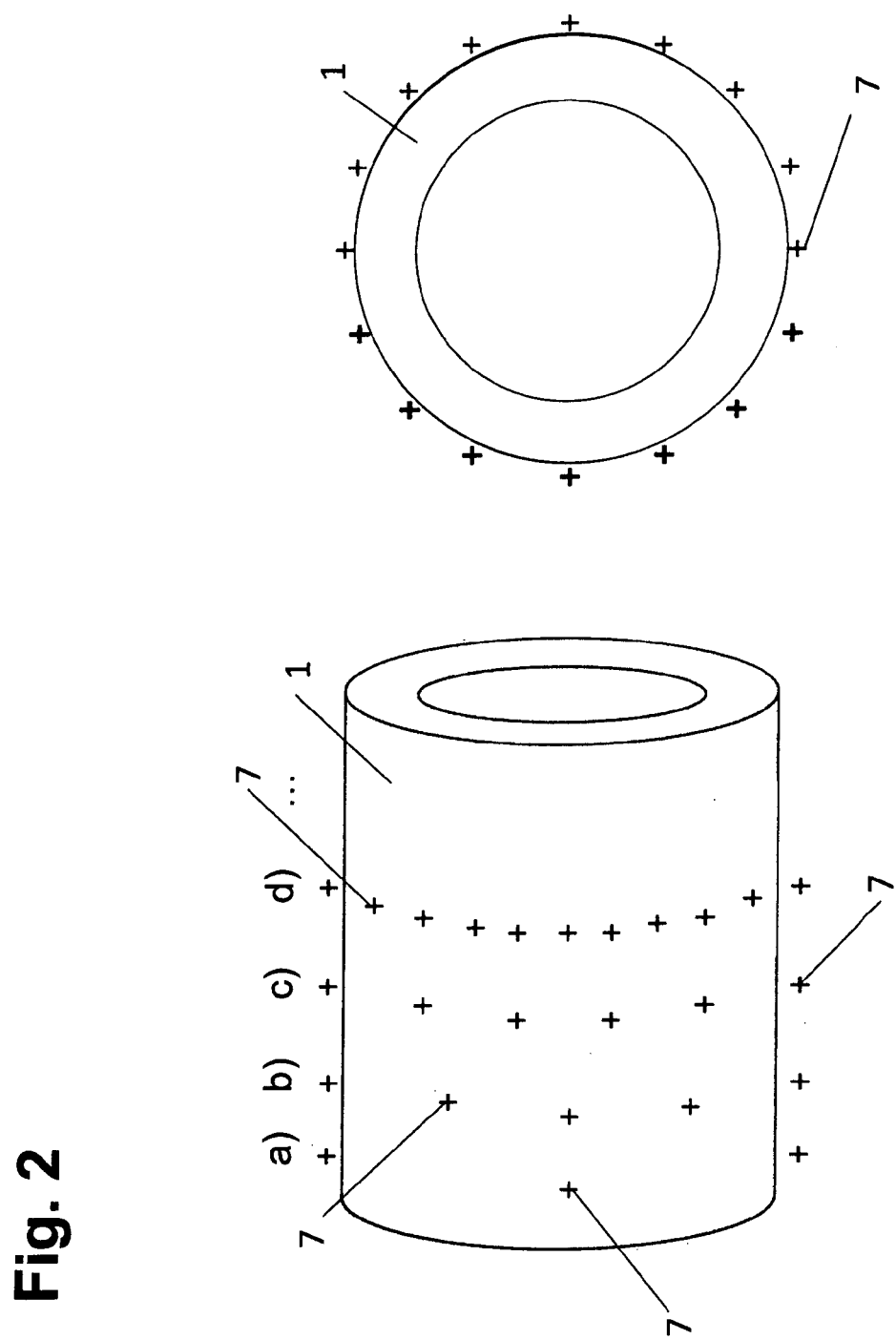
FIG. 2 shows examples of the distribution of the testing heads or measurement points around the circumference of a pipe.

FIG. 2 shows possible distributions of the positions of the measurement points or the positions of the testing head arrangements 7 shown in FIG. 1 around the circumference of a pipe 1 for this purpose. The more densely the cross-shaped testing head arrangements 7 are placed along the circumference of the pipe, the higher the lateral resolution along the pipe circumference. FIG. 2 shows four different distributions of the testing head arrangements 7 or measurement points on a pipe 1 as an example in the left partial image for this purpose, which are identified with a) to d). A higher density of the measurement points or testing head arrangements 7 results in a higher resolution. In the right part of the figure, such an arrangement is illustrated once again in section through the pipe 1. In this case, the possibility also exists of only covering one-half or also only one-fourth of the pipe with the testing heads, if symmetrical strain of the pipe exists. In the event of asymmetrical strain, the testing heads are to be distributed around the entire circumference of the pipe, as indicated in FIG. 2. If it is to be expected that inhomogeneous strains will occur on the pipeline along the pipe axis, these inhomogeneous strains are thus also detected by the use of multiple testing head belts along the pipe axis.

The cross-shaped arrangement of the testing heads shown in FIG. 1 can optionally also be simplified by omitting the separate transmission-reception arrangements having the testing heads 3a, 3b, 4a, 4b.

In this case, however, no items of information about local stresses along the pipe axis can then be obtained. Of course, however, it is possible to detect the relative stress changes over the wall thickness of the pipe wall.

Figure 3:
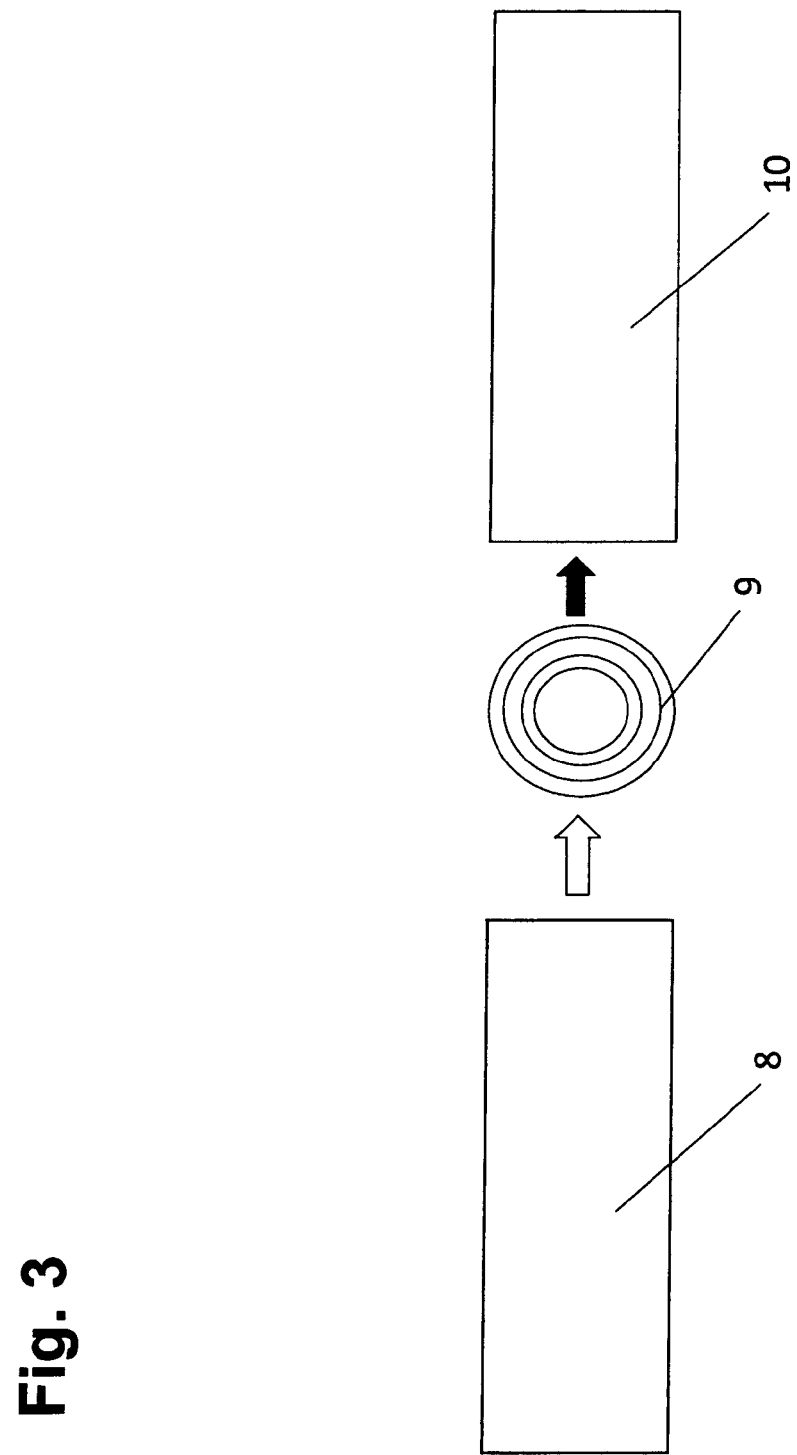
FIG. 3 shows a schematic illustration of the determination of the stresses or stress gradients over a layer model of a pipeline.

FIG. 3 schematically shows the procedure during the determination of the stresses or stress gradients on the pipe inner side on the basis of a layer model. In this schematically indicated layer model 9, the pipe wall is divided into various layers, as indicated in the figure. The measured eddy current impedances, the measured ultrasound runtimes, amplitudes, the temperature curve ascertained from the temperature measurement, and the stress curve ascertained from the temperature measurement are used as the model input variables 8. The layer model 9 then delivers layer-related eddy current impedances, layer-related ultrasound runtimes, amplitudes, and a layer-related stress curve as the model output variables 10, wherein the stress curve on the innermost layer of the layer model corresponds to the stresses or stress gradients on the inner side of the pipe.

Figure 4:
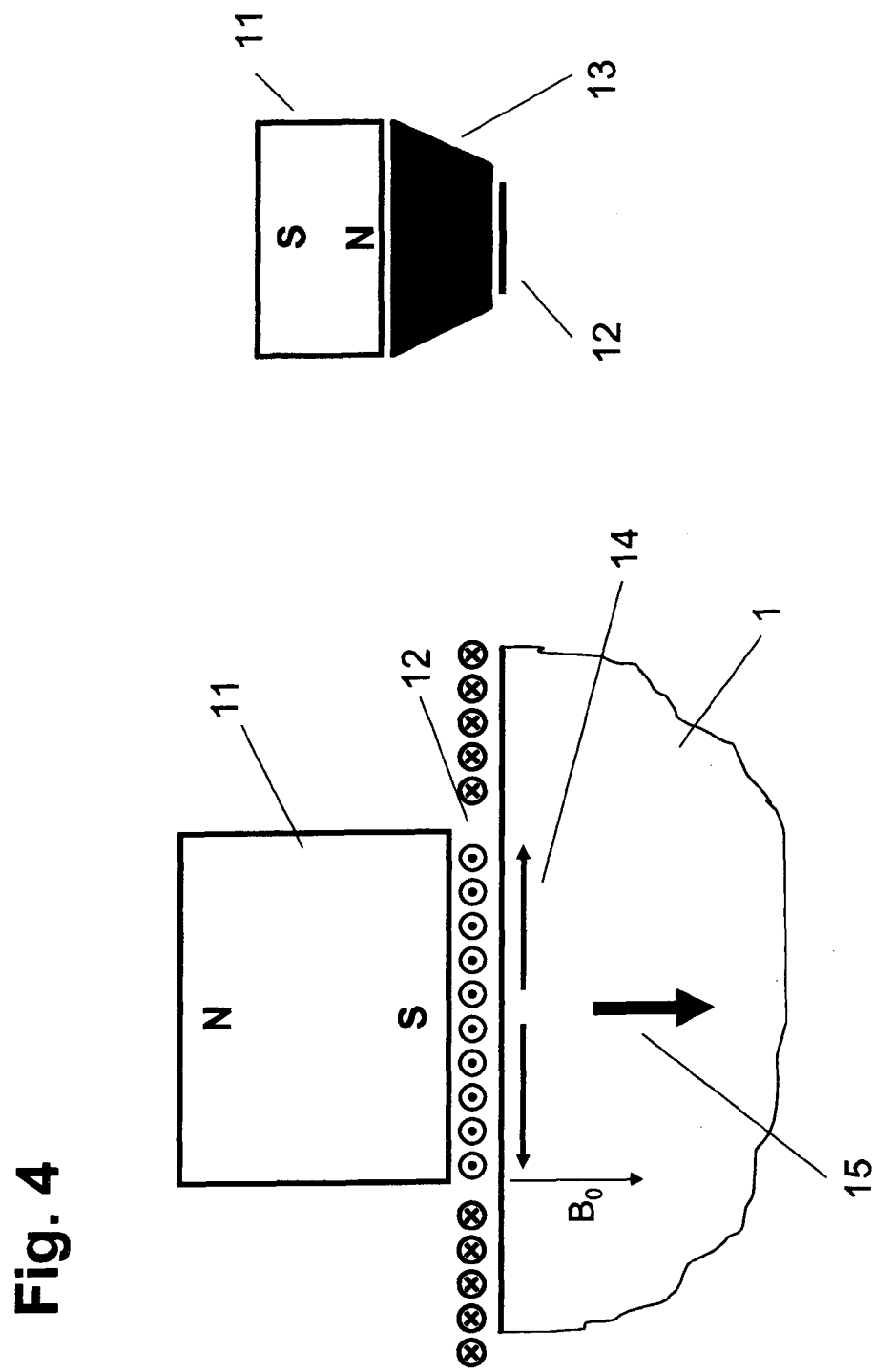
FIG. 4 shows an example of a structure of one of the testing heads for generating a linearly polarized transverse wave which is introduced perpendicularly.

FIGS. 4 to 7 show examples of ultrasound transducers or testing heads as can be used in the proposed method. The figures show that different transducer types can be used for the ultrasound runtime and amplitude measurement and also for the measurement of the eddy current impedances. FIG. 4 shows an example of the construction of an ultrasound transducer, which generates linearly polarized transverse waves which are introduced perpendicularly. The transducer has a magnet 11 above an HF coil 12. The magnet can be both a permanent magnet—as shown in the figure—and also an electromagnet. A static magnetic field $B_0$ is generated in the pipe wall by the magnet, as indicated in the figure. Via the AC voltage at the HF coil 12, which is recognizable in the illustrated cross section, an ultrasound wave is excited in the pipe wall, the oscillation direction or polarization 14 and propagation direction 15 of which are also indicated in the figure. As can be seen in the right part of the figure, an additional concentrator 13 for amplifying the static magnetic field can also be used between the HF coil 12 and the magnet 11.

Figure 5:
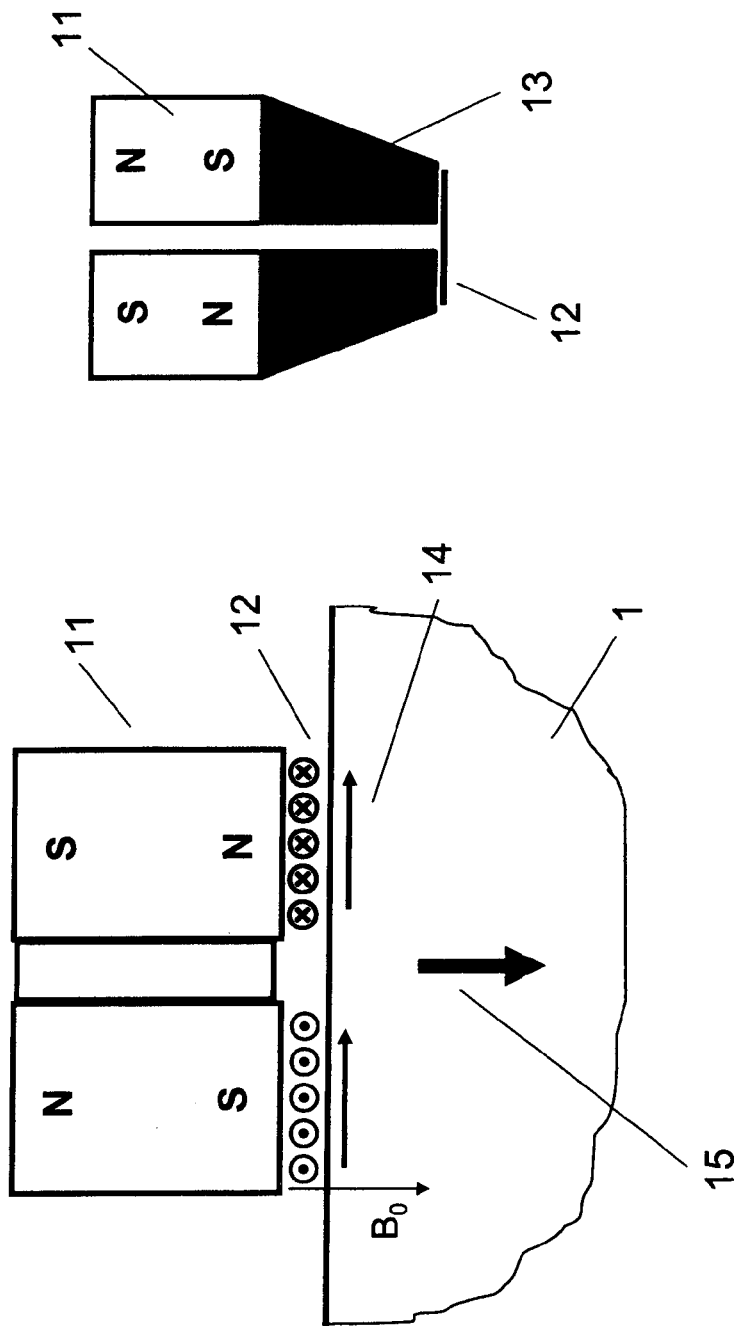
FIG. 5 shows a further example of the structure of a testing head for generating a linearly polarized transverse wave which is introduced perpendicularly.

An alternative embodiment of such an ultrasound transducer for introducing a linearly polarized transverse wave perpendicularly is illustrated in FIG. 5. In this example, two magnets 11 are used above the HF coil 12.

Figure 6:
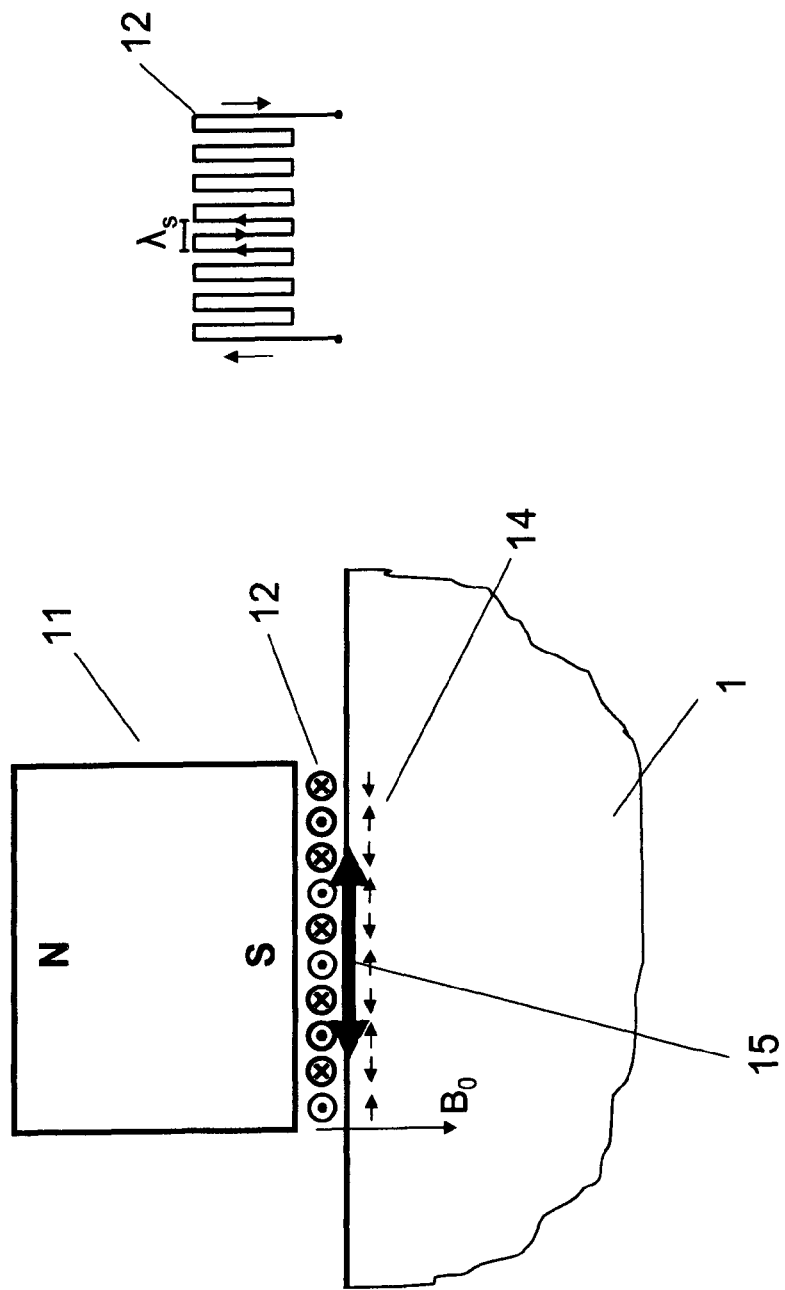
FIG. 6 shows an example of the structure of a testing head for generating a Rayleigh wave.

FIG. 6 shows an example of the structure of an electromagnetic ultrasound transducer, using which Rayleigh waves are generated. In this transducer, a meandering HF coil 11 is used, which can be seen in the right part of the figure in a top view. The propagation direction 15 of the ultrasound wave and the oscillation direction 14 of the ultrasound wave are also indicated in the figure.

An example of an ultrasound transducer for generating a horizontally polarized transverse wave is shown in FIG. 7. In this ultrasound transducer, permanent magnets 11 having alternating polarization are used in a periodic arrangement, as can be seen from the figure. An ultrasound wave is then generated via the HF coil 12 located underneath, the propagation direction 15 of which along the pipe surface is again schematically illustrated in the figure.

The transducers of FIGS. 4 to 7 are known from the prior art, so that the structure and functionality thereof will not be discussed in greater detail here.

An eddy current impedance measurement can be implemented at different frequencies and therefore different penetration depths into the pipeline using each individual one of the illustrated ultrasound transducers. The eddy current impedance measurement can be carried out in this case using the HF coil of the transducer, which is also used for generating ultrasound. However, it is also possible, of course, to arrange a separate HF coil on the transducer for such an eddy current measurement.

LIST OF REFERENCE NUMERALS 1 pipeline
2 temperature sensor
3a ultrasound transducer (transmitter)
3b ultrasound transducer (receiver)
4a ultrasound transducer (transmitter)

4b ultrasound transducer (receiver)
5 ultrasound transducer (transmitter/receiver)
6 ultrasound transducer (transmitter/receiver)
7 testing head arrangement
8 model input variables
9 layer model
10 model output variables
11 magnet
12 HF coil
13 concentrator
14 oscillation direction/polarization
15 propagation direction of the ultrasound wave

The invention claimed is:

1. A method for detecting temporally varying thermomechanical stresses and stress gradients over a wall thickness of metal bodies, in particular pipelines, in which a temperature is measured at at least one measurement point on an outer surface of a body and additional measurements are carried out using electromagnetic ultrasound transducers in a region of the measurement point to determine the one or more of stresses or stress gradients over the wall thickness of the body via the measured temperature from the additional measurements, wherein a temperature curve between an inner surface and the outer surface is ascertained from the measured temperature and is used for the determination of the one or more of stresses or stress gradients over the wall thickness of the body from the additional measurements;

characterized in that one or more of ultrasound runtime, amplitude, or eddy current impedance measurements are carried out using the electromagnetic ultrasound transducers, wherein the one or more of stresses or stress gradients are determined by analyzing the one or more of ultrasound runtime, amplitude, or eddy current impedance measurements in conjunction with the measured temperature or the ascertained temperature curve; and characterized in that the determination of the one or more stresses or stress gradients is performed on the basis of a layer model of a wall of the body, which uses the ascertained temperature curve and a stress curve derived therefrom as well as measured and temperature-corrected ultrasound runtimes, amplitudes, and eddy current impedances as input variables and supplies layer-related ultrasound runtimes, amplitudes, eddy current impedances, and stress curves as output variables, wherein the layer-related stress curves are determined by iterative optimization of the layer model from the layer-related ultrasound runtimes, amplitudes, and eddy current impedances.

2. The method as claimed in claim 1, characterized in that two linearly polarized transverse waves, which are perpendicular to one another, are emitted perpendicularly into a wall of the body in each case using the electromagnetic ultrasound transducers, to measure ultrasound runtimes and amplitudes in pulse echo operation.

3. The method as claimed in claim 2, characterized in that, during the measurement on a pipe as the body, one of the transverse waves is linearly polarized in an axial direction of the pipe and the other is linearly polarized in a circumferential direction of the pipe.

4. The method as claimed in claim 2, characterized in that two pairs of electromagnetic ultrasound transducers in separate transmission-reception arrangement are additionally used, which generate Rayleigh waves or horizontally polarized transverse waves, wherein the two pairs are arranged at an angle of 90° in relation to one another at the measurement point.

5. The method as claimed in claim 1, characterized in that the electromagnetic ultrasound transducers are used at multiple measurement points distributed over an external surface.

* * * * *